United States Patent [19]

Horn et al.

[11] Patent Number: 5,071,875
[45] Date of Patent: Dec. 10, 1991

[54] SUBSTITUTED 2-AMIDOTETRALINS AS MELATONIN AGONISTS AND ANTAGONISTS

[75] Inventors: Alan S. Horn, RA Noordhorn, Netherlands; Margarita L. Dubocovich, Evanston, Ill.

[73] Assignee: Northwestern University, Evanston, Ill.

[21] Appl. No.: 411,675

[22] Filed: Sep. 25, 1989

[51] Int. Cl.$^5$ .................. A61K 31/165; A61K 31/16; C07C 233/65; C07C 233/63

[52] U.S. Cl. .................................... 514/613; 514/616; 514/617; 514/619; 514/624; 514/625; 514/628; 514/629; 564/153; 564/155; 564/157; 564/184; 564/189; 564/190; 564/192; 564/211; 564/218; 564/222

[58] Field of Search ............... 564/222, 184, 153, 155, 564/157, 189, 190, 192, 211, 218; 514/629, 613, 617, 624, 616, 619, 625, 628

[56] References Cited

U.S. PATENT DOCUMENTS

| 4,035,512 | 7/1977 | Sugihara et al. | 564/184 |
|---|---|---|---|
| 4,091,018 | 5/1978 | Asato | 564/222 |
| 4,107,206 | 8/1978 | Hewett et al. | 564/222 |
| 4,254,268 | 3/1981 | Strong | 564/222 |
| 4,320,148 | 3/1982 | DeMarinis | 564/222 |

FOREIGN PATENT DOCUMENTS

| 0637364 | 7/1983 | Switzerland | 564/184 |
|---|---|---|---|

OTHER PUBLICATIONS

Arendt, J. et al., Br. Med. J., 292:1170 (1986).
Arendt, J., Oxford Reviews of Reproductive Biology, 8:266-320 (1986).
Besharse, J. C., Progress in Retinal Research, 1:81-124 (1982).
Beyer, H., Chem. Berichte, 70:1101-1110 (1937).
Birau, N., Melatonin-Current Status and Perspectives, 297-326 (1985).
Birkeland, A. J., Neuroendocrinology, 34:126-131 (1982).
Cardinali, D. P., Endocrinol. Rev., 2:327-346 (1981).
Cassone, V. M., et al., Journal of Biological Rhythms, 1:219-229 (1986).
Darrow, J. M., et al., Journal of Biological Rhythms, 1:39-54 (1985).
Dubocovich, M. L., The Journal of Pharmacology and Experimental Therapeutics, 246:902-910 (1988).
Dubocovich, M. L., FASEB, 2:2765-2773 (1988).
Dubocovich, M. L., et al., Proc. Nat'l. Acad. Sci. USA, 84:3916-3920 (1987).
Dubocovich, M. L., The Journal of Pharmacology and Experimental Therapeutics, 234:395-401 (1985).
Dubocovich, M. L., European Journal of Pharmacology, 105:193-194 (1984).
Dubocovich, M. L., Nature, 306:782-784 (1983).
Duncan, M. J., et al., Endocrinology, 125:1011-1018 (1989).
Ferrier, I. N., et al., Clinical Endocrinology, 17:181-187 (1982).
Fine, S. A., et al., J. Org. Chem., 32:4132 (1967).
Hacksell, U., et al., J. Med. Chem., 22:1469-1475 (1979).
Heward, C. B., et al., Life Sciences, 17:1167-1178 (1975).
Horn, A. S., et al., Eur. J. Med. Chem., 23:325-328 (1988).
Horn, A. S., et al., J. Med. Chem., 21:825-828 (1978).
Iguchi, H., et al., J. Clin. Endocrinol. & Metab., 55:27-29 (1982).
Iuvone, P. M., The retina: A Model for Cell Biology Studies, 2:1-72 (1986).
Jimerson, D. C., et al., Life Sciences, 20:1501-1508 (1977).
Kauppila, A., et al., J. Clin. Endocrinol. & Metab., 65:823-828 (1987).
Krauss, G., et al., Inv. Ophthalm. Vis. Sci. vol. 26, Abst. 49 (1988).
Lewy, A. J., Science, 235:352-354 (1987).
Lewy, A. J., et al., Proceedings of the Society for Experimental Biology and Medicine, 183:11-18 (1986).
Maestroni, G. J. M., et al., Clin. Exp. Immunol., 68:384-391 (1987).
Menaker, M., Vertebrate Circadian Systems, 1-12 (1982).
Minneman, K. P., et al., Life Sci., 17:1189-1200 (1975).
Redman, J., et al., Science, 219:1089-1091 (1983).
Reppert, S. M., et al., Science, 242:78-81 (1988).
Rosenthal, N. E., et al., Arch. Gen. Psychiatric, 41:72-80 (1984).
Smith, J. A., et al., J. Pharmacol., 31:246-248 (1979).
Smythe, G. A., et al., Nature (London), 244:230-231 (1973).
Stanberry, L. R., Endocrinology, 113:469-475 (1983).
Tamarkin, L., et al., Science, 227:714-720 (1985).
Tamarkin, L., et al., Science, 216:1003-1005 (1982).
Underwood, H., et al., Physiology & Behavior, 35:267-270 (1985).
Vriend, J., Med. Hypotheses, 4:376-387 (1978).
Weinstock, J., et al., J. Med. Chem., 29:1615-1627 (1986).
Wetterberg, L., Neural Transm., 13:289-310 (1978).
Condon, M. et al., "Phenylpiperazinotetrahydronaphthols and derivatives", CA, vol. 94, 139840h (1981) +10$^{th}$ Collect Index.
Ames et al., "The Synthesis of Alkoxy-1,2,3,4-tetrahydronaphthalene Derivatives Part I etc.", J. Chem. Soc. 2636, Apr. 1965.

Primary Examiner—Richard L. Raymond
Assistant Examiner—Susan P. Treanor
Attorney, Agent, or Firm—Tilton, Fallon, Lungmus & Chestnut

[57] ABSTRACT

The present invention relates generally to compounds having melatonin receptor activities and in particular to substituted 2-amidotetralin derivatives; to pharmaceutical preparations comprising such compounds; and to methods for using these compounds as therapeutic and diagnostic reagents.

7 Claims, No Drawings

SUBSTITUTED 2-AMIDOTETRALINS AS MELATONIN AGONISTS AND ANTAGONISTS

BACKGROUND OF THE INVENTION

The present invention relates generally to compounds having melatonin receptor activities and in particular to substituted derivatives of 2-amidotetralins, to pharmaceutical preparations comprising these compounds; to methods for using these compounds as therapeutic agents and to methods for using these compounds as diagnostic reagents.

Melatonin (N-acetyl-5-methoxytryptamine) is a hormone synthesized and secreted primarily by the pineal gland, with highest levels occurring during the dark period of a circadian light-dark cycle. The hormone is also found in the retina, and gut. The structure of melatonin is:

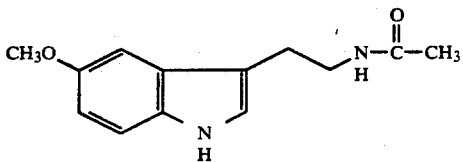

Melatonin is involved in the transduction of photoperiodic information and appears to modulate a variety of neural and endocrine functions in vertebrates, including the regulation of reproduction, body weight and metabolism in photoperiodic mammals, the control of circadian rhythms and the modulation of retinal physiology. Retinal melatonin has been implicated in photoreceptor outer segment disc shedding and phagocytosis, in melanosome aggregation in pigment epithelium, and cone photoreceptor retinomotor movement. Of the various physiological processes that have been associated with melatonin, those best substantiated are its effects on sexual maturation, ovarian function, and chronobiological rhythms. See Arendt, J., Oxford Reviews of Reproductive Biology, Vol. 8: 266-320 (1986) and Dubocovich, M. L., FASEB J., 2:2765-2773 (1988).

Exogenous melatonin administration has been found to synchronize circadian rhythms in rats. Cassone, et al., J. Biol. Rhythms, 1:219-229 (1986). In humans, administration of melatonin has been used to treat jet-lag related sleep disturbances, considered to be caused by desynchronization of circadian rhythms. Arendt, et al., Br. Med. J., 292:1170 (1986). Classically, the physiological effects of endogenous melatonin have been antagonized by exposure of animals to light, which inhibits the synthesis of melatonin, or by removal of the pineal gland.

Pharmacological studies have shown that picomolar concentrations of melatonin selectively inhibit the calcium-dependent release of dopamine from rabbit and chicken retina through activation of a site having the pharmacological and functional characteristics of a receptor. Dubocovich, M. L., Nature, 306:782-784 (1983). Dubocovich, M. L., Eur. J. Pharmacol., 105:193-194 (1984). Dubocovich, M. L., J. Pharmacol. Exp. Ther., 234:395-401 (1985). Using the radioiodinated ligand, 2-[$^{125}$I]iodomelatonin, which enhances the ability to detect melatonin receptor sites in vertebrate retina, a pharmacological correlation between the binding site labeled by 2-[$^{125}$I]iodomelatonin and a functional response regulated by melatonin in the chicken and rabbit retina has been demonstrated. Dubocovich, M. L., et al., Proc. Nat'l. Acad. Sci. USA, 84:3916 (1987). Using this radioligand, melatonin binding sites have been localized primarily in the suprachiasmatic nucleus and pars tuberalis/median eminence of mammals, including humans. Reppert, et al., Science, 242:78-81 (1988) and Duncan, et al., Endocrinol., 125:1011-1018 (1989). This is interesting because the melatonin receptor sites localized in the suprachiasmatic nucleus and/or median eminence/par tuberalis have been suggested to regulate circadian rhythms and reproductive function.

While the radioligand 2-[$^{125}$I] iodomelatonin is a useful probe for the localization and characterization of melatonin receptors, a significant problem in further elucidating the mechanism of action of melatonin is the lack of potent and selective melatonin receptor agonists and antagonists. Such agonists/antagonists could find application not only in the study of melatonin receptor interactions but also in the treatment of conditions possibly affected by melatonin activity, such as depression, jet-lag, disturbances in the sleep-wakefulness cycle, hypertension, glaucoma, reproduction and neuroendocrine disorders.

Generally, agonists of neurotransmitters and neurohormones are structurally related to the transmitter they mimic, whereas antagonists may be structurally unrelated and quite diverse. The term melatonin agonist is used herein to comprise compounds that mimic melatonin activity, e.g., melatonin inhibition of the calcium-dependent release of [$^3$H]dopamine evoked by electrical stimulation of chicken retina and rabbit retina. To date, all of the known melatonin agonists are derivatives of melatonin itself, e.g., 2-iodomelatonin, 6-chloromelatonin, 6,7-dichloro-2-methyl melatonin, and 8-hydroxymelatonin, and all contain the 5-methoxy indole ring system as an essential moiety. See, Dubocovich, et al., Proc. Nat'l. Acad. Sci. (USA), 84:3916-3918 (1987). Dubocovich, J. Pharmacol. Exp. Ther., 234:395 (1985).

As for melatonin antagonists, previous structure-activity studies on the melatonin receptor led to the suggestion that N-acetyltryptamine analogs lacking the 5-methoxy group might be potential melatonin receptor antagonists. Heward, et al., Life Sci., 17:1167-1178 (1975). Dubocovich, M. L., Eur. J. Pharmacol., 105:193 (1984). Dubocovich, et al., Proc. Nat'l. Acad. Sci. (USA), 84:3916 (1987). Dubocovich, M. L., J. Pharmacol. Exp. Ther., 234:395 (1985). However, while N-acetyltryptamine was reported to antagonize the melatonin-induced lightening of the α-melanocyte stimulating hormone-induced darkening of the frog skin, and to be a competitive melatonin receptor antagonist in chicken retina, it was found to be a partial melatonin agonist in rabbit retina. Heward, C. B., et al., Life Sci., 17:1167 (1975); Dubocovich, M. L., Eur. J. Pharmacol., 105:193 (1984). Dubocovich, M. L., J. Pharmacol. Exp. Ther., 234:395 (1985).

The first compound shown to be a competitive antagonist of mammalian melatonin receptors was luzindole (2-benzyl-N-acetyltryptamine). Dubocovich, M. L., J. Pharmacol. Exp. Ther., 246:902 (1988). Luzindole, in concentrations up to 10 μM, does not modify either the spontaneous outflow or the calcium-dependent release of [$^3$H]dopamine, but does antagonize the ability of melatonin to inhibit [$^3$H]dopamine release in a competitive fashion. A variety of other compounds have been examined for possible antagonistic activity; however, none have shown the competitive antagonism seen with luzindole.

All of these known melatonin agonists and antagonists retain the 5-melatonin-indole ring system of the natural hormone melatonin. Historically, development of receptor agonists and antagonists which are chemically unrelated to the natural hormone or neurotransmitter has led to selective and potent therapeutic agents. However, there continues to exist a need in the art for such melatonin agonists and antagonists for use in investigating the physiological role of the hormone melatonin, and in treating disorders involving disturbances of the melatonin system. The present invention describes a non-indolic class of compounds which surprisingly show high melatonin agonist/antagonist activity.

BRIEF SUMMARY OF THE INVENTION

The compounds of the invention have the general formula:

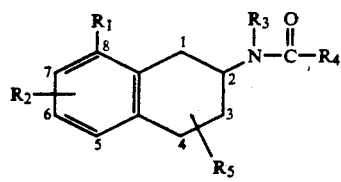

wherein:
$R_1$ is hydrogen, halogen, amino, amido, a $C_{1-4}$ alkyl, alkoxyl, or alkoxylaryl;
$R_2$ is hydrogen, hydroxyl, halogen, amino, amido, aryl, mono- or di- $C_{1-4}$ alkylamino, $C_{1-4}$ alkylaryl, or alkoxylaryl, or $C_{1-4}$ alkyl, alkenyl, alkynyl, alkoxyl;
$R_3$ is hydrogen, aryl, $C_{1-4}$ alkylaryl, or $C_{1-4}$ alkyl, alkenyl, or alkynyl;
$R_4$ is aryl, $C_{1-4}$ alkylaryl, or $C_{1-4}$ alkyl, haloalkyl, or cycloalkyl;
$R_5$ is hydrogen, hydroxyl, halogen, oxo, aryl, $C_{1-4}$ alkylaryl, or $C_{1-4}$ alkyl;
wherein aryl substitutents of $R_2$, $R_3$, $R_4$, and $R_5$ may optionally be halogen, hydroxyl, amino, mono- or di- $C_{1-4}$ alkylamino, or $C_{1-4}$ alkyl or alkoxyl substituted, provided that when $R_1$ is methoxy, and $R_2$, $R_3$, and $R_5$ are hydrogen, $R_4$ is not methyl.

Compounds of the invention contain at least one asymmetric carbon atom, i.e., $C_2$ and as a result comprise racemic mixtures of both enantiomeric forms. The properties of the compounds may, to a greater or lesser extent, be ascribed to either steroisomer. Thus, the pure enantiomers, as well as the racemic mixtures thereof, are within the scope of the invention. For compounds containing two asymmetric carbon atoms, and therefore occurring as cis or trans isomers, it is understood that the invention encompasses both isomers.

Preferred compounds include: 8-methoxy-2-propionamido-tetralin; 2-chloroacetamido-tetralin; 8-methoxy-2-n-butyramido-tetralin; 8-methoxy-2-cyclopropanecarbonylamido-tetralin; 8-methoxy-2-chloroacetamido-tetralin; 4-phenyl-2-acetamido-tetralin; 4-phenyl-2-propionamido-tetralin; 4-benzyl-2-acetamidotetralin; 4-phenyl-2-chloroacetamido-tetralin; and 4-benzyl-2-propionamido-tetralin.

Compounds of the invention exhibit strong melatonin receptor activity and are expected to be useful in methods for treating disorders which arise from a disturbed functioning of the melatonin system. Thus, also provided by the invention are methods for treatment of disorders associated with abnormal melatonin activity in an organism wherein a therapeutically effective amount of a composition is administered comprising a compound of the formula:

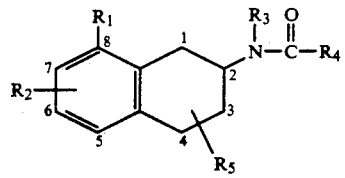

wherein:
$R_1$ is hydrogen, halogen, amino, amido, a $C_{1-4}$ alkyl, alkoxyl, or alkoxylaryl;
$R_2$ is hydrogen, hydroxyl, halogen, amino, amido, aryl, mono- or di- $C_{1-4}$ alkylamino, $C_{1-4}$ alkylaryl, or alkoxylaryl, or $C_{1-4}$ alkyl, alkenyl, alkynyl, alkoxyl;
$R_3$ is hydrogen, aryl, $C_{1-4}$ alkylaryl, or $C_{1-4}$ alkyl, alkenyl, or alkynyl;
$R_4$ is aryl, $C_{1-4}$ alkylaryl, or $C_{1-4}$ alkyl, haloalkyl, or cycloalkyl;
$R_5$ is hydrogen, hydroxyl, halogen, oxo, aryl, $C_{1-4}$ alkylaryl, or $C_{1-4}$ alkyl;
wherein aryl substitutents of $R_2$, $R_3$, $R_4$, and $R_5$ may optionally be halogen, hydroxyl, amino, mono- or di- $C_{1-4}$ alkylamino, or $C_{1-4}$ alkyl or alkoxyl substituted.

Preferred compounds for this method include those where $R_1$ is hydrogen or alkoxyl, where $R_2$ is hydrogen or alkoxyl, where said alkoxyl is preferably methyl, where $R_3$ is preferably hydrogen, and where $R_4$ is preferably methyl, chloromethyl, ethyl, propyl, cyclopropyl, n-butyl, iso-butyl, phenyl, or benzyl; and/or where $R_5$ is phenyl or benzyl. Specifically, preferred compounds are those having melatonin receptor activity including: 8-methoxy-2-acetamido-tetralin; 8-methoxy-2-propionamido-tetralin; 2-chloroacetamidotetralin; 8-methoxy-2-n-butyramido-tetralin; 8-methoxy-2-cyclopropanecarbonylamido-tetralin; 8-methoxy-2-chloroacetamido-tetralin; 4-phenyl-2-acetamido-tetralin; 4-phenyl-2-propionamido-tetralin; 4-benzyl-2-acetamidotetralin; 4-phenyl-2-chloroacetamido-tetralin; and 4-benzyl-2-propionamido-tetralin.

Presently preferred compounds for use in a method for blocking melatonin function by administering a melatonin antagonist include: 4-phenyl-2-acetamidotetralin; 4-phenyl-2-propionamido-tetralin; and 4- phenyl-2-chloroacetamido-tetralin. Presently preferred compounds for use in a method for mimicking melatonin function by administering a melatonin agonist include: 8-methoxy-2-acetamido-tetralin; 8-methoxy-2- propionamido-tetralin; 2-chloroacetamido-tetralin; 8- methoxy-2-n-butyramido-tetralin; 8-methoxy-2-cyclopropanecarbonylamido-tetralin; 8-methoxy-2-chloroacetamido-tetralin; 4-benzyl-2-acetamido-tetralin; and 4-benzyl-2-propionamido-tetralin.

Also provided by the invention are pharmaceutical compositions comprising pharmaceutically effective amounts of one or more compounds of the invention in combination with an inert pharmaceutical carrier, as well as methods for producing a melatonin-like action, or alternatively blocking the effects of melatonin, by administering these pharmaceutical compositions. Generally, where it is desirable to inhibit melatonin function, those compounds of the invention having melatonin antagonist activity are administered; where it is desirable to mimic melatonin function, those compounds having melatonin agonist activity are administered. Some compounds (i.e., partial agonists) may show either agonist or antagonist activity depending not only on the activity of the melatonergic system at the time of administration, but also upon both the dose and route of administration. The route of administration can be any that produces the desired effect and includes for example oral, intra-venous, intra-muscular, and topical applications, including, e.g., time release transdermal patches.

In one preferred embodiment of the present invention, a therapeutically effective amount of one or more of the compounds of the invention can be administered to treat chronobiological disorders, such as, seasonal affective disorder (SAD), sleep disorders, and symptoms, such as drowsiness and fatigue, associated with disturbances in sleep/wake cycles (e.g., jet-lag, workers on night shifts, etc.), or to treat glaucoma by lowering intra-ocular pressure. Therapeutically effective amounts of one or more compounds of the invention can be administered to treat various psychiatric disorders related to altered melatonin function or influenced by melatonin and circadian rhythms, e.g., affective disorders (mania and depression), alcoholism, stress, aging (dementia such as Alzheimer's disease), epilepsy, convulsions, anxiety, tremors induced by idiopathic parkinsonism, and adventitious movements induced by L-dopa movements; or to treat various neuroendocrine disorders related to altered melatonin function or influenced by melatonin and biological rhythms (e.g., peptic ulceration, psoriasis, hair tonic, and body weight) particularly relating to regulation of reproductive maturation and function e.g., idiopathic delayed puberty, sudden infant death (SID), premature labor, infertility, antifertility, premenstrual syndrome, and sexual dysfunction (i.e., impotence and decreased orgasmic activity). In addition, compounds of the invention can be used alone, or in combination, in animals to manipulate breeding cycles, body weight, coat color and oviposition and can be used as ovulation or sperm production inhibitors to control the population of suceptible hosts, including insects, birds, and animals.

Also provided by the invention is a method for localizing melatonin receptors in for example, a tissue sample, wherein the sample is incubated with a compound of the invention and wherein the compound is labelled with a marker, the marker is detected and the melatonin receptors in the sample are thereby localized.

Other aspects and advantages of the present invention will be apparent upon consideration of the following detailed description thereof which includes numerous illustrative examples of the practice of the invention.

DETAILED DESCRIPTION OF THE INVENTION

The following examples 1 through 26 are intended to be illustrative of practice of the present invention rather than limiting thereon. Examples 1–22 describe the synthesis of the compounds of the invention. Examples 23–25 provide the results obtained from the pharmacological testing of the compounds of the invention. Specifically, example 23 provides the results obtained with the compounds of the invention in an assay that measures the inhibition of 2-[$^{125}$I]iodomelatonin binding using chicken retinal membranes; example 24 provides the results obtained in an assay to ascertain which test compounds mimic the melatonin-induced inhibition of the release of [$^3$H]dopamine from rabbit retina membranes; example 25 provides the results obtained in an assay to measure the potential antagonistic activity of the test compounds during the melatonin-induced inhibition of [$^3$H]dopamine release from rabbit retina.

Example 26 relates to pharmaceutical preparations comprising the compounds of the invention, to methods for using these compounds as therapeutic agents in treating disorders associated with abnormal melatonin activity, and to methods for using the compounds as diagnostic reagents.

SYNTHESIS OF COMPOUNDS OF THE INVENTION

The compounds of the invention are synthesized as described in Examples 1–22 below. Table 1 provides: the example number which describes the synthesis of the compound; the reference number and name of each compound; and the substituents: $R_1$, $R_2$, $R_3$, $R_4$, and $R_5$ for each compound. The general formula for the compounds synthesized is given below.

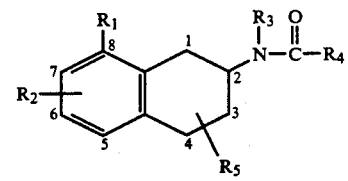

TABLE 1

| EXAMPLE | COMPOUND AND REFERENCE NUMBER | $R_1$ | $R_2$ | $N(R_3)$—$C(O)$—$R_4$ | $R_5$ |
|---|---|---|---|---|---|
| 2 | AH001 8-methoxy-2-acetamido-tetralin | OCH$_3$ | H | NHC(O)CH$_3$ | H |
| 1 | AH002 8-methoxy-2-propionamido-tetralin | OCH$_3$ | H | NHC(O)C$_2$H$_5$ | H |
| 10 | AH005 2-acetamido-tetralin | H | H | NHC(O)CH$_3$ | H |
| 11 | AH006 2-propionamido-tetralin | H | H | NHC(O)C$_2$H$_5$ | H |
| 3 | AH007 8-methoxy-2-benzoylamido-tetralin | OCH$_3$ | H | NHC(O)benzyl | H |
| 8 | AH008 7-methoxy-2-acetamido-tetralin | H | OCH$_3$ | NHC(O)CH$_3$ | H |
| 12 | AH010 2-phenylacetamido-tetralin | H | H | NHC(O)benzyl | H |
| 13 | AH011 2-chloroacetamido-tetralin | H | H | NHC(O)CH$_2$Cl | H |
| 4 | AH013 8-methoxy-2-n-butyramido-tetralin | OCH$_3$ | H | NHC(O)C$_3$H$_7$ | H |
| 5 | AH014 8-methoxy-2-iso-butyramido-tetralin | OCH$_3$ | H | NHC(O)CH(CH$_3$)$_2$ | H |
| 6 | AH015 8-methoxy-2-cyclopropanecarbonylamido-tetralin | OCH$_3$ | H | NHC(O)C$_3$H$_5$ | H |
| 7 | AH016 8-methoxy-2-phenylacetamido-tetralin | OCH$_3$ | H | NHC(O)benzyl | H |
| 16 | AH017 8-methoxy-2-chloroacetamido-tetralin | OCH$_3$ | H | NHC(O)CH$_2$Cl | H |
| 9 | AH018 5-methoxy-2-acetamido-tetralin | H | OCH$_3$ | NHC(O)CH$_3$ | H |
| 14 | AH019 2-benzoylamido-tetralin | H | H | NHC(O)phenyl | H |
| 15 | AH020 2-butyramido-tetralin | H | H | NHC(O)C$_3$H$_7$ | H |

TABLE 1-continued

| EXAMPLE | COMPOUND AND REFERENCE NUMBER | | $R_1$ | $R_2$ | SUBSTITUENTS $N(R_3)$—C(O)—$R_4$ | $R_5$ |
|---|---|---|---|---|---|---|
| 17 | AH023 | 4-phenyl-2-acetamido-tetralin | H | H | NHC(O)CH$_3$ | phenyl |
| 18 | AH024 | 4-phenyl-2-propionamido-tetralin | H | H | NHC(O)C$_2$H$_5$ | phenyl |
| 20 | AH025 | 4-benzyl-2-acetamido-tetralin | H | H | NHC(O)CH$_3$ | benzyl |
| 19 | AH026 | 4-phenyl-2-chloroacetamido-tetralin | H | H | NHC(O)CH$_2$Cl | phenyl |
| 21 | AH027 | 4-benzyl-2-propionamido-tetralin | H | H | NHC(O)C$_2$H$_5$ | benzyl |
| 20d | AH028 | 4-benzyl-2-acetamido-1-tetralin | H | H | NHC(O)CH$_3$ | benzyl |
| 22 | AH029 | 4-benzyl-2-chloroacetamido-tetralin | H | H | NHC(O)CH$_2$Cl | benzyl |

The three methods used for synthesis of the compounds of the invention are as follows.

METHOD 1

The appropriately substituted 2-tetralone is converted to the corresponding 2-aminotetralin by condensation with benzylamine, catalytic reduction over platinum, and subsequent debenzylation over palladium-charcoal. The resulting primary amine is then reacted with the appropriate acyl chloride or acid anhydride to yield the desired amide. Horn, A. S., et al., *J. Med. Chem.*, 21:825 (1978). The following amides were synthesized utilizing the indicated reactants:

| Amide | Substituted 2-tetralone | Acid anhydride/ Acyl Chloride |
|---|---|---|
| AH 001 | 8-methoxy-2-tetralone | acetic anhydride |
| AH 002 | 8-methoxy-2-tetralone | propionic anhydride |
| AH 005 | 2-tetralone | acetic anhydride |
| AH 006 | 2-tetralone | propionic anhydride |
| AH 007 | 8-methoxy-2-tetralone | benzoyl chloride |
| AH 008 | 7-methoxy-2-tetralone | acetic anhydride |
| AH 010 | 2-tetralone | phenylacetyl chloride |
| AH 011 | 2-tetralone | chloroacetyl chloride |
| AH 013 | 8-methoxy-2-tetralone | butyric anhydride |
| AH 014 | 8-methoxy-2-tetralone | isobutyryl chloride |
| AH 015 | 8-methoxy-2-tetralone | cyclopropanecarbonyl chloride |
| AH 016 | 8-methoxy-2-tetralone | phenylacetyl chloride |
| AH 017 | 8-methoxy-2-tetralone | chloroacetyl chloride |
| AH 018 | 5-methoxy-2-tetralone | acetic anhydride |
| AH 019 | 2-tetralone | benzoyl chloride |
| AH 020 | 2-tetralone | butyric anhydride |
| AH 023 | 4-phenyl-2-tetralone | acetic anhydride |
| AH 024 | 4-phenyl-2-tetralone | propionic anhydride |
| AH 026 | 4-phenyl-2-tetralone | chloroacetyl chloride |

METHOD 2

The appropriately substituted 1-tetralone is converted to its oxime and this compound is treated with p-toluenesulfonyl chloride to yield the O-(p-tolylsulfonyl)oxime. Treatment of the latter compound with sodium ethoxide in benzene produces the keto-amine via the Neber rearrangement. Acylation of this derivative with the appropriate acyl halide or acid anhydride yields the corresponding keto-amide. Catalytic reduction of this intermediate over palladiumcharcoal yields the desired end product. Horn, A. S., et al., *Eur. J. Med. Chem.*, 23:325 (1988). Weinstock, J., et al., *J. Med. Chem.*, 29:1615 (1986). The following amides were synthesized according to method 2 utilizing the reactants specified.

| Amide | Substituted 1-tetralone | Acid anhydride/ Acyl chloride |
|---|---|---|
| AH 025 | 4-benzyl-1-tetralone | acetic anhydride |
| AH 027 | 4-benzyl-1-tetralone | propionic anhydride |
| AH 028 | 4-benzyl-1-tetralone | acetic anhydride |
| AH 029 | 4-benzyl-1-tetralone | chloroacetyl chloride |

METHOD 1

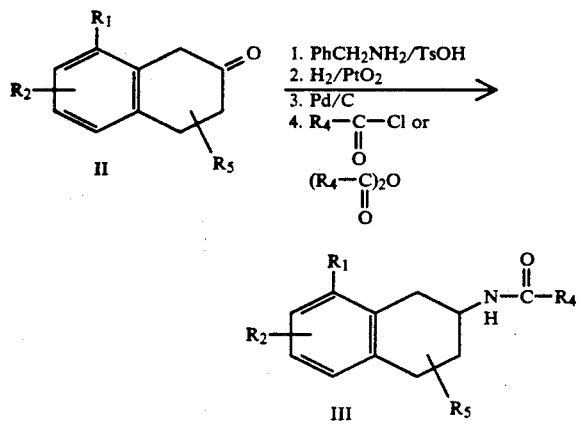

METHOD 2

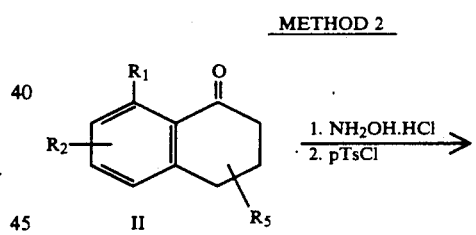

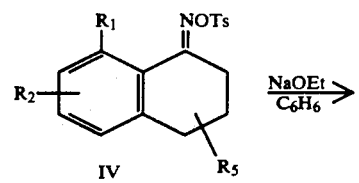

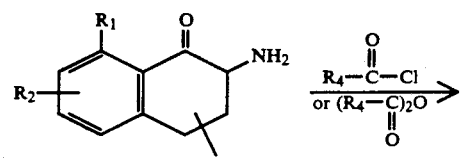

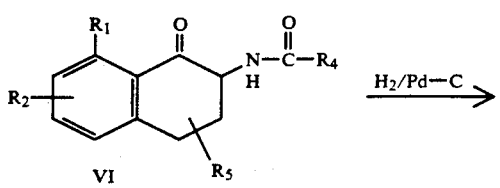

-continued
METHOD 2

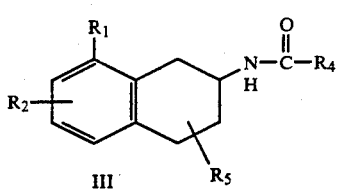

The synthesis of analogues having various $R_3$ substituents is achieved through standard variations of the method described in the examples below, i.e., using one of the two general methods 1 or 2 to obtain the appropriately substituted intermediate which is then acylated using the appropriate $R_4$ substituted acid chloride or anhydride. The synthesis of analogues having various $R_4$ substituents is shown in general method 3.

METHOD 3

The appropriately substituted 2-tetralone is treated with the corresponding $R_3$ substituted amine; the resulting intermediate is reduced; and the final product is obtained by acylation with the appropriate acid chloride or anhydride. Hacksell, U., et al., *J. Med. Chem.*, 22:1469 (1979).

METHOD 3

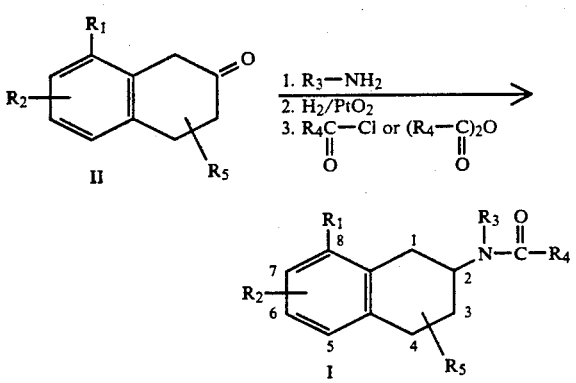

EXAMPLE 1

Preparation of 8-methoxy-2-propionamidotetralin [AH 002]

To a solution of 8-methoxy-2-tetralone (5.30 g, 30.1 mmol) in 50 ml of benzene, benzylamine (4.30 g, 40 mmol) and p-toluenesulfonic acid (0.1 g) were added. The mixture was then refluxed for 1 hr under an atmosphere of nitrogen gas using a Dean and Stark apparatus. The benzene and other volatiles were removed under reduced pressure and 45 ml of absolute alcohol was added to the residue. After transfer to a Parr hydrogenation flask, platinum oxide (50 mg) was added and the mixture was hydrogenated for 2.5 hr under a hydrogen pressure of 2 atmospheres. After filtration of the mixture and removal of the ethanol under reduced pressure, a brown oil was obtained. This oil was diluted with ethyl acetate (25 ml) and then a solution of ether/HCl was added dropwise to yield the HCl salt of 8-methoxy-2-benzylaminotetralin (7.20 g, 79%). Three grams (9.9 mmol) of this salt was converted to the free base by treatment with a solution of sodium carbonate. The base was extracted into ether which was then dried and evaporated under reduced pressure to yield a brown oil The latter was dissolved in absolute alcohol (60 ml) and hydrogenated in a Parr flask over palladiumcharcoal (1.6 g) for 1 hr at 2-atmospheres. Following an isolation procedure similar to that described above, 8-methoxy-2-aminotetralin HCl (1.17 g, 55%) was isolated.

m.p. 281°–282° C.
I.R. (KBr) 3160 cm$^{-1}$ 2420 cm$^{-1}$ (NH$_3{}^+$) 2060 cm$^{-1}$ (NH$_3{}^+$).
M.S. (chemical ionization, NH$_3$ gas) m/e 178 (M+1).

To a solution of 8-methoxy-2-aminotetralin HCl (0.30 g, 1.40 mmol) in ethyl acetate (15 ml) water (5 ml) and sodium acetate (0.65 g), propionic anhydride (1.15 ml) was added and the mixture was stirred well for 6 hr. Water (10 ml) was then added and after shaking the aqueous and organic layers were separated. The aqueous layer was extracted with ethyl acetate and the combined ethyl acetate layers were washed with saturated solutions of sodium bicarbonate and sodium chloride and then dried (MgSO$_4$) and evaporated under reduced pressure to yield a white solid. Recrystallization (methanol/ethyl acetate) yielded 0.10 g (31%) of a white crystalline material.

m.p. 151°–152° C.
I.R. (KBr) 3315 cm$^{-1}$ (NH) 1640 cm$^{-1}$ (C=O).
M.S. (chemical ionization, NH$_3$ gas) m/e 234 (M+1).

EXAMPLE 2

Preparation of 8-methoxy 2-acetamido-tetralin [AH 001]

Using a procedure similar to that described in Example 1, 0.30 g of 8-methoxy-2-amino-tetralin yielded 0.23 g (69%) of 8-methoxy-2-acetamido-tetralin following treatment with acetic anhydride.

m.p. 156°–157° C.
I.R. (KBr) 1640 cm$^{-1}$ (C=O)
M.S. (chemical ionization, NH$_3$ gas) m/e 220 (M+1).

EXAMPLE 3

Preparation of 8-methoxy-2-benzoylamido-tetralin [AH 007]

Using a procedure similar to that described in Example 1, 0.40 g of 8-methoxy-2-amino-tetralin yielded 0.44 g (84%) of 8-methoxy-2-benzoylamido-tetralin following treatment with benzoyl chloride.

m.p. 173°–175° C.
I.R. (KBr) 1625 cm$^{-1}$ (C=O).
M.S. (chemical ionization, NH$_3$ gas) m/e 282 (M+1).

EXAMPLE 4

Preparation of 8-methoxy-2-n-butyramidotetralin [AH 013]

Using a procedure similar to that described in Example 1, 0.22 g of 8-methoxy-2-aminotetralin yielded 0.16 g (63%) of 8-methoxy-2-n-butyramidotetralin following treatment with n-butyric anhydride.

m.p. 139°–140° C.
I.R. (KBr) 3300 cm$^{-1}$ (NH) 1630 cm$^{-1}$ (C=O).
M.S. (chemical ionization, NH$_3$ gas) m/e 248 (M+1).

EXAMPLE 5

Preparation of 8-methoxy-2-iso-butyramido-tetralin [AH 014]

Using a procedure similar to that described in Example 1, 0.22 g of 8-methoxy-2-amino-tetralin yielded 0.18 g (71%) of 8-methoxy-2-iso-butyramido-tetralin following treatment with iso-butyryl chloride.
m.p. 167°-168° C.
I.R. (KBr) 1635 cm$^{-1}$ (C=O).
M.S. (chemical ionization, $NH_3$ gas) m/e 248 (M+1).

EXAMPLE 6

Preparation of 8-methoxy-2-cyclopropanecarbonylamido-tetralin [AH 015]

Using a procedure similar to that described in Example 1, 0.20 g of 8-methoxy-2-amino-tetralin yielded 0.19 g (83%) of 8-methoxy-2-cyclopropane-carbonylamidotetralin following treatment with cyclopropanecarbonyl chloride.
m.p. 185°-187° C.
I.R. (KBr) 1630 cm$^{-1}$ (C=O).
M.S. (chemical ionization, $NH_3$ gas) m/e 246 (M+1).

EXAMPLE 7

Preparation of 8-methoxy-2-phenylacetamido-tetralin [AH 016]

Using a procedure similar to that described in Example 1, 0.24 g 8-methoxy-2-amino-tetralin yielded 0.20 g (61%) of 8-methoxy-2-phenylacetamido-tetralin following treatment with phenylacetyl chloride.
m.p. 154°-156° C.
I.R. (KBr) 1630 cm$^{-1}$ (C=O).
M.S. (chemical ionization, $NH_3$ gas) m/e 296 (M+1).

EXAMPLE 8

Preparation of 7-methoxy-2-acetamido-tetralin [AH 008]

Using a procedure similar to that described in Example 1, 0.40 g of 7-methoxy-2-amino-tetralin yielded 0.21 g (51%) of 7-methoxy-2-acetamido-tetralin following treatment with acetic anhydride.
m.p. 105°-108° C.
I.R. (KBr) 1625 cm$^{-1}$ (C=O).
M.S. (chemical ionization, $NH_3$ gas) m/e 220 (M+1).

EXAMPLE 9

Preparation of 5-methoxy-2-acetamido-tetralin [AH 018]

Using a procedure similar to that described in Example 1, 0.30 g of 5-methoxy-2-amino-tetralin yielded 0.06 g (20%) of 5-methoxy-2-acetamido tetralin following treatment with acetic anhydride.
m.p. not determined
I.R. (KBr) 1625 cm$^{-1}$ (C=O).
M.S. (chemical ionization, $NH_3$ gas) m/e 220 (M+1).

EXAMPLE 10

Preparation of 2-acetamidotetralin [AH 005]

Using a procedure similar to that described in Example 1, 1.50 g of 2-amino-tetralin yielded 1.01 g (65%) of 2-acetamido-tetralin following treatment with acetic anhydride.
m.p. 109°-111° C.
I.R. (KBr) 1630 cm$^{-1}$ (C=O).
M.S. (chemical ionization, $NH_3$ gas) m/e 190 (M+1).

EXAMPLE 11

Preparation of 2-propionamido-tetralin [AH 006]

Using a procedure similar to that described in Example 1, 0.26 g of 2-amino-tetralin yielded 0.25 g (86%) of 2-propionamido-tetralin following treatment with propionic anhydride.
m.p. 99°-101° C.
I.R. (KBr) 1635 cm$^{-1}$ (C=O).
M.S. (chemical ionization, $NH_3$ gas) m/e 204 (M+1).

EXAMPLE 12

Preparation of 2-phenylacetamido-tetralin [AH 010]

Using a procedure similar to that described in Example 1, 0.45 g of 2-amino-tetralin yielded 0.47 g (72%) of 2-phenylacetamido-tetralin following treatment with phenylacetyl chloride.
m.p. 119°-121° C.
I.R. (KBr) 1625 cm$^{-1}$ (C=O).
M.S. (chemical ionization, $NH_3$ gas) m/e 266 (M+1).

EXAMPLE 13

Preparation of 2-chloroacetamido-tetralin [AH 011]

Using a procedure similar to that described in Example 1, 0.38 g of 2-amino-tetralin yielded 0.26 g (56%) of 2-chloroacetamido-tetralin following treatment with chloroacetyl chloride.
m.p. 131°-133° C.
I.R. (KBr) 1650 cm$^{-1}$ (C=O).
M.S. (chemical ionization, $NH_3$ gas) m/e 224 (M+1).

EXAMPLE 14

Preparation of 2-benzoylamido-tetralin [AH 019]

Using a procedure similar to that described in Example 1, 0.40 g of 2-amino-tetralin yielded 0.38 g (69%) of 2-benzoylamido-tetralin following treatment with benzoyl chloride.
m.p. 154°-156° C.
I.R. (KBr) 1625 cm$^{-1}$ (C=O).
M.S. (chemical ionization, $NH_3$ gas) m/e 252 (M+1).

EXAMPLE 15

Preparation of 2-butyramido-tetralin [AH 020]

Using a procedure similar to that described in Example 1, 0.24 g of 2-amino-tetralin yielded 0.23 g (81%) of 2-butyramido-tetralin following treatment with butyric anhydride.
m.p. 78°-81° C.
I.R. (KBr) 1630 cm$^{-1}$ (C=O).
M.S. (chemical ionization, $NH_3$ gas) m/e 218 (M+1).

EXAMPLE 16

Preparation of 8-methoxy-2-chloroacetamidotetralin [AH 017]

To a solution of 8-methoxy-2-amino-tetralin HCl (0.16 g, 0.75 mmol) in dichloromethane (10 ml) and in sodium hydroxyde (0.2 g) in water (2 ml), was added chloroacetyl chloride (2 ml) and the mixture was stirred for 6 hr. The reaction was then poured into water (25 ml) and the organic layer was separated. The aqueous layer was extracted with dichloromethane and the combined organic layers were then shaken with a solution of sodium bicarbonate, dried over $MgSO_4$ and then evaporated to yield a white solid. After recrystallization (acetone/hexane) 0.12 g (63%) of 8-methoxy-2-chloracetamidotetralin was obtained.

m.p. 136°–139° C.
I.R. (KBr) 3270 cm$^{-1}$ (NH) 1640 cm$^{-1}$ (C=O).
M.S. (chemical ionization, NH$_3$ gas) m/e 254 (M+1).

EXAMPLE 17

Preparation of 4-phenyl-2-acetamidotetralin [AH 023]

a. 4-Phenyl-2-benzylaminotetraline HCl

To a solution of 4.20 g (19.1 mmol) of 4-phenyl-2-tetralone (Fine and Stern, *J. Org. Chem.*, 32:4132 (1967)) in 35 ml of benzene, were added, 1.95 g (18.3 mmol) of benzylamine and a crystal of p-toluenesulfonic acid. The reaction mixture was refluxed under an atmosphere of nitrogen for one hour with continual removal of water via a Dean and Stark trap. Removal of all volatiles under reduced pressure yielded an oil (5.75 g). This oil was dissolved in 50 ml of a mixture of tetrahydrofuran and methanol (15:1). The pH was then adjusted to between 4 and 5 with dry ether-HCl. The precipitate was removed by filtration and 1550 mg of sodiumcyanoborohydride was added to the resulting solution. This mixture was stirred and warmed to 40° C. and kept at this temperature for 20 hrs. Occasional adjustments of the pH were necessary. The course of the reaction was followed by the disappearance of the imine peak at 1625 cm$^{-1}$ in the I.R. spectrum.

The reaction mixture was poured into water and made basic with sodium carbonate. After extraction with ether, drying over magnesium sulfate and decolorization with charcoal, the organic extracts were evaporated under reduced pressure to yield an oil (5.0 g). Conversion to an HCl salt yielded 2.91 g (44%) of 4-phenyl-2-benzylaminotetraline HCl. Recrystallization gave a white crystalline product.

m.p. 204.5°–206° C.
I.R. (KBr) 2920–2300 cm$^{-1}$ (NH$_3^+$)
M.S. (chemical ionization, NH$_3$ gas) m/e 314 (M+1).

b. 4-Phenyl-2-aminotetralin HCl

Three hundred eighty mg (0.82 mmol) of the free base of 4-phenyl-2-benzylaminotetraline was dissolved in 10 ml of ethanol and to which was added 250 mg Pd/C (10%). This mixture was shaken in a Parr apparatus under a pressure of 3 atm. of hydrogen at 35° C. for 3 hrs and for a further 18 hrs at room temperature. After removal of the catalyst and evaporation of the organic solvent, an oil was obtained. Conversion to an HCl salt gave 140 mg (40%) of 4-phenyl-2-aminotetralin HCl.

m.p. 237°–237.7° C.
I.R. (KBr) 3100–2400 cm$^{-1}$ (NH$_3^+$)
M.S. (chemical ionization, NH$_3$ gas) m/e 224 (M+1).

c. 4-Phenyl-2-acetamidotetralin

To a solution of 180 mg (0.80 mmol) of 4-phenyl-2-aminotetraline HCl in 3.5 ml ethyl acetate and 2.0 ml water, was added 360 mg of sodium acetate. To this mixture 0.6 ml of acetic anhydride was then added and the mixture was stirred for 24 hrs. The addition of 2 ml of water resulted in the formation of two layers. After separation, the water layer was extracted twice with ethyl acetate. The combined organic layers were washed 3 times with a saturated solution of sodium bicarbonate and once with a saturated solution of sodium chloride. After drying over magnesium sulfate, the organic solution was evaporated under reduced pressure to yield 4-phenyl-2-acetamidotetralin as a white solid (170 mg, 79%).

m.p. 176°–177.6° C.
I.R. (KBr) 3270 cm$^{-1}$ (NH) 1630 and 1550 cm$^{-1}$ (C=O).
M.S. (chemical ionization, NH$_3$ gas) m/e 266 (M+1).

EXAMPLE 18

Preparation of 4-phenyl-2-propionamido-tetralin [AH 024]

Using a procedure similar to that described in Example 17, 100 mg of 4-phenyl-2-amino-tetralin yielded 40 mg (32%) of 4-phenyl-2-propionamido tetralin following treatment with propionic anhydride.

m.p. 144°–146° C.
I.R. (KBr) 1640 cm$^{-1}$ (C=O).
M.S. (chemical ionization, NH$_3$ gas) m/e 280 (M+1).

EXAMPLE 19

Preparation of 4-phenyl-2-chloroacetamido-tetralin [AH 026]

Using a procedure similar to that described in Example 17, 130 mg of 4-phenyl-2-amino-tetralin yielded 10 mg (6%) of 4-phenyl-2-chloroacetamido-tetralin following treatment with chloroacetyl chloride.

m.p. 189°–190° C.
I.R. (KBr) 1640 cm$^{-1}$ (C=O).
M.S. (chemical ionization, NH$_3$ gas) m/e 300 (M+1).

EXAMPLE 20

Preparation of 4-benzyl-2-acetamidotetralin [AH 025]

a. 4-Benzyl-1-tetralon oxime

To 63.3 g (0.7 mol) of 4-benzyl-1-tetralone (Beyer, *Chem. Berichte*, 70:1101 (1937)) dissolved in 500 ml ethanol, was added 80 g (1.15 mol) of hydroxylamine HCl and 80 g (0.98 mol) of sodium acetate. The mixture was refluxed for 2.5 hrs and then poured into 1.2 L water. After filtration, the white solid was washed with ice-cold water until the pH of the filtrate was 6–7. The product was recrystallized from ethanol yielding 57.5 g (85%).

m.p. 142.6°–143.5° C.
I.R. (KBr) 3200 cm$^{-1}$ (OH), 1590 cm$^{-1}$ (C=N).
M.S. (chemical ionization, NH$_3$ gas) m/e 252 (M+1).

b. 4-Benzyl-1-tetralon-O-(p-toluenesulfonil)oxime

The above oxime (48.5 g, 0.19 mol) was dissolved in 190 ml dry pyridine and then cooled to 0° C. A solution of 150 g (0.78 mol) of p-toluenesulfonyl chloride in 230 ml dry pyridine was added dropwise over 45 min and then left to stir for a further 18 hrs at 0° C. The orange colored reaction mixture was poured into 1.5 L icewater and the resulting yellowish precipitate was filtered and washed with water and ice-cold ethanol. The product was recrystallized from ethyl acetate to yield 65 g (84%).

m.p. 159°–160° C.
I.R. (KBr) 1590 cm$^{-1}$ (Ar, C=N), 1370 cm$^{-1}$, 1180 cm$^{-1}$ (SO$_2$).
M.S. (chemical ionization, NH$_3$ gas) m/e 406 (M+1).

c. 2-Amino-4-benzyl-1-tetralone HCl

To a solution of potassium t-butoxide (6.08 g, 54.2 mmol) dissolved in 60 ml of "super-dry" ethanol at 0° C. under nitrogen, was added, dropwise over 45 min, a solution of 20 g (49.4 mmol) of the above tosyloxime in 360 ml dry toluene. The reaction mixture was stirred for 2 hrs at 0°–4° C. and for 2 hrs at 10–15° C. After filtration, the filtrate was acidified with 14 ml 36% hydrochloric acid and stirred for 16 hrs at room temperature.

The product was filtered and washed twice with 25 ml cold acetone. The filtrate was reduced in volume to obtain a further fraction of the product. Total yield 12.65 g (89%).

m.p. the substance decomposed above 180° C.

I.R. (KBr) 3180 cm$^{-1}$ (NH$_3$+) 1680 cm$^{-1}$ (C=O).

M.S. (chemical ionization, NH$_3$ gas) m/e 252 (M+1). AH 028 d. 2-Acetamido-4-benzyl-1-tetralone

Eight g (27.8 mmol) of the above keto-amine HCl was dissolved in ethyl acetate. To this solution was added 20.7 g (0.15 mol) sodium acetate, 25 ml water and 16.7 ml acetic anhydride. This mixture was stirred for 2 hrs at room temperature. Fifty ml of water were added and after 30 min of stirring, the organic layer was separated and washed with 50 ml of water and 100 ml of saturated NaCl solution. After evaporation under reduced pressure, the resulting oil was dissolved in 40 ml of toluene and refluxed for 30 min using a Dean and Stark trap. Removal of the solvent gave an oil which slowly crystallized giving 6.5 g (80%) of a white solid. Recrystallization from ethanol yielded the product as a white crystalline material.

m.p. 142°-143° C.

I.R. (KBr) 3380 cm$^{-1}$ (NH) 1695 cm$^{-1}$ (C=O) 1630 cm$^{-1}$ (C=O, amide).

M.S. (chemical ionization, NH$_3$ gas) m/e 294 (M+1).

e. 4-Benzyl-2-acetamidotetralin

Two g (6.8 mmol) of the above keto-amide was dissolved in 30 ml of acetic acid. To this solution, were added 1.4 ml 70% HClO$_4$ and 340 mg 10% Pd/C. Hydrogenation was carried out for 16 hrs at room temperature under 3 atmospheres of hydrogen. After filtration, the filtrate was evaporated to yield an oil. This oil was dissolved in 150 ml of water and then neutralized with sodium bicarbonate. This solution was extracted twice with dichloromethane (150 ml). The dichloromethane extracts were then shaken with a saturated solution of sodium chloride. After drying over magnesium sulfate, the solvent was removed to yieldan oil. This oil was dissolved in dry ether. This resulting solution yielded a white crystalline product, 1.33 g (70%).

m.p. 168°-168.5° C.

I.R. (KBr) 3280 cm$^{-1}$ (NH) 1625 cm$^{-1}$ (C=O).

M.S. (chemical ionization, NH$_3$ gas) m/e 280 (M+1).

EXAMPLE 21

Preparation of 4-benzyl-2-propionamido-tetralin [AH 027]

Using a procedure similar to that described in Example 20d, 500 mg of 2-propionamido-4-benzyl-1-tetralone yielded 180 mg (38%) of 4-benzyl-2-propionamido-tetralin following catalytic reduction.

m.p. 148°-149° C.

I.R. (KBr) 1650 cm$^{-1}$ (C=O).

M.S. (chemical ionization, NH$_3$ gas) m/e 294 (M+1).

EXAMPLE 22

Preparation of 4-benzyl-2-chloroacetamido-tetralin [AH 029]

Using a procedure similar to that described in Example 20d, 500 mg of 2-chloroacetamido-4-benzyl-1-tetralone yielded 130 mg (28%) of 4-benzyl-2-chloroacetamido-tetralin following catalytic reduction.

m.p. 151°-152° C.

I.R. (KBr) 1665 cm$^{-1}$ (C=O).

M.S. (chemical ionization, NH$_3$ gas) m/e 314 (M+1).

PHARMACOLOGICAL STUDIES

Two types of in vitro tests, specific for melatonin-like activity, were used for evaluating the pharmacological activities of the synthesized compounds and are described below in Examples 23–25.

The first test, described in Example 23, measures the ability of a test compound to inhibit 2-[$^{125}$I]iodomelatonin binding to a site exhibiting the pharmacological characteristics of a melatonin receptor in chicken retinal membranes. If a compound shows high activity (i.e., a low IC$_{50}$) in inhibiting the binding of 2-[$^{125}$I]iodomelatonin to the melatonin binding site, this demonstrates the compound's ability to interact with the melatonin binding site; however, such activity does not establish whether the test compound is an agonist or an antagonist. Examples 24 and 25, respectively, describe tests to establish agonist or antagonist activity.

The Example 24 assay ascertains whether a test compound mimics the melatonin-induced inhibition of the release of [$^3$H]dopamine from rabbit retina membranes. In this assay, the test compound is added before the second period of stimulation (S$_2$) and its effect is compared to that of melatonin. The IC$_{50}$ value obtained is that concentration of test compound required to inhibit, by 50%, the calcium-dependent release of [$^3$H]dopamine. The lower the IC$_{50}$, the greater the agonistic activity; that is, the closer the value is to the IC$_{50}$ obtained using melatonin, the more closely the compound is said to mimic melatonin activity.

Example 25 utilizes a similar assay with a modification to determine whether a test compound antagonizes the melatonin-induced inhibition of the release of [$^3$H]dopamine from rabbit retina membranes. In this example, the test compound is added before the first period of electrical stimulation (S$_1$) and remains present until the end of the experiment. In this modification, melatonin at different concentrations is added before the second period of stimulation to ascertain whether the test compound, which is present during both S$_1$ and S$_2$, has the capacity to antagonize the action of melatonin. These assays are described in greater detail below.

EXAMPLE 23

Inhibition of 2-[$^{125}$I]Iodomelatonin binding

It has been shown that 2-[$^{125}$I]iodomelatonin binds with high affinity to a site exhibiting the pharmacological characteristics of a melatonin receptor in chicken retinal membranes. In this assay, i.e., in chicken retinal membranes, 2-[$^{125}$I]-iodomelatonin selectively labels melatonin binding sites and shows no binding to alpha- and beta-adrenergic, serotonin, or dopamine sites, as agents that affect these sites do not compete for 2-[$^{125}$I]-iodomelatonin binding. Dubocovich, et al., Proc. Nat'l. Acad. Sci. (USA), 84:3916 (1987). The test compounds were assayed for their possible melatonin agonist or antagonist-like activity, using an in vitro chicken retinal membrane preparation as described in Dubocovich, et al., Proc. Nat'l. Acad. Sci. (USA), 84:3916 (1987).

2-[$^{125}$I]iodomelatonin was diluted in Tris-HCl buffer (50 mM) with 0.01% bovine serum albumin. The compounds to be tested were dissolved in 1 mM HCl with 0.1% bovine serum albumin. Binding was initiated by addition of 220-μl aliquots of retinal membranes resuspended in the Tris-HCl buffer to tubes containing 20 μl of test compound or vehicle, and radioligand. The binding of 2-[$^{125}$I] iodomelatonin was routinely measured in duplicate after incubation at 0° C. for 5 hr in the dark. Reactions were terminated by addition of 5 ml of ice-cold Tris-HCl buffer, and the contents were immediately filtered through glass-fiber filters (Schleicher & Schuell no. 30) soaked in 0.5% (vol/vol) polyethylenimine solution. Each filter was washed twice with 5 ml of the cold buffer. Radioactivity was determined in a gamma counter. In a typical experiment, total 2-[$^{125}$I]iodomelatonin (67 pM) binding was 2542±361 cpm (n=3), and the non-specific binding defined with 3 μM 6-chloromelatonin was 350±35 cpm (n=3). The total radioactivity bound to filters represented 166±10 cpm (n=3).

The IC$_{50}$ is that concentration of a compound required to competively inhibit the specific binding of [$^{125}$I]iodomelatonin by 50%. The results in Table 2 demonstrate that several compounds, in particular AH 001, AH 002, AH 013, and AH 017, AH 023, AH 024, AH 025, AH 026, AH 027, and AH 029 show high activity (low IC$_{50}$) in competitively inhibiting the binding of 2-[$^{125}$I]iodomelatonin to the melatonin binding site. This ability to competitively inhibit 2-[$^{125}$I]iodomelatonin demonstrates that these compounds interact with melatonin binding sites.

TABLE 2

Inhibition of 2-[$^{125}$I]iodomelatonin Binding to Chicken Retinal Membranes

| Compound | IC$_{50}$(nM) |
|---|---|
| 2-Iodomelatonin | 2.5 |
| 6-Chloromelatonin | 4.0 |
| Melatonin | 6.3 |
| AH 001 | 860 |
| AH 002 | 61 |
| AH 005 | 20,000 |
| AH 006 | 13,000 |
| AH 007 | >10,000 |
| AH 008 | >10,000 |
| AH 010 | >100,000 |
| AH 011 | 20,000 |
| AH 013 | 257 |
| AH 014 | 4,620 |
| AH 015 | 2,943 |
| AH 016 | >100,000 |
| AH 017 | 682 |
| AH 018 | 16,000 |
| AH 019 | >10,000 |
| AH 020 | 2,908 |
| AH 023 | 630 |
| AH 024 | 250 |
| AH 025 | 400 |
| AH 026 | 250 |
| AH 027 | 790 |
| AH 028 | 25,000 |
| AH 029 | 300 |

EXAMPLE 24

Assay to Ascertain Which Test Compounds Mimic the Melatonin-Induced Inhibition of [$^3$H]-dopamine Release from Rabbit Retina Membranes Melatonin and related indoles are capable of inhibiting the calcium-dependent release of [$^3$H]dopamine from chicken retina and from rabbit retina. Dubocovich, J. Pharm. Exp. Ther., 234:395-401 (1985). The amount of inhibition, by a test compound, of the calcium-dependent release of [$^3$H]dopamine is therefore a useful measure of whether a compound is a melatonin agonist. In other words, a test compound is characterized as an agonist if its presence results in an inhibition of [$^3$H]dopamine release.

Compounds inhibiting dopamine release may exert that affect by activating D-2 dopamine autoreceptors rather than melatonin receptors. Accordingly, all experiments were run in the presence of S-sulpiride (0.1 μM) to block D-2 dopamine autoreceptors present in the dopamine amacrine cells of retina.

IC$_{50}$ values are the concentration of test compound required to inhibit, by 50%, the calcium-dependent release of [$^3$H]dopamine. Thus, the lower the IC$_{50}$, the greater the agonistic activity.

Assays were performed as described in Dubocovich, J. Pharm. Exp. Ther., 234:395-401 (1985). Retinal tissues are incubated for 10 min at 37° C. in the presence of 0.1 μM [$^3$H]dopamine. The tissue was then washed in Krebs' solution at 37° C. and transferred to individual cylindrical plastic tubes having a thin nylon mesh on the bottom. These plastic tubes were then transferred to individual glass superfusion chambers containing platinum electrodes 30 mm apart. The tissue samples are superfused with Krebs' solution, starting at time equal zero until a leveling off of the spontaneous release of radioactivity occurred (about 60 mins). A time equal 60 mins S$_1$ is applied. Melatonin, or the test compound, is added 20 mins after S$_1$ and was present throughout the remainder of the experiment. The second stimulation (S$_2$) is applied 20 mins after the addition of melatonin or of the test compound.

Tritium release, i.e., release of [$^3$H]dopamine, was elicited by field stimulation at 3 Hz, 20 mA, 2 msec duration. Field stimulations were applied in each experiment at either 60 (S$_1$) or 100 (S$_2$), min after the end of the incubation with [$^3$H]dopamine. Samples of the superfusate were collected before, during, and after the period of stimulation. At the end of each experiment, the retinal tissue contained in each chamber was solubilized and the tritium content remaining in the retinal tissue was determined by liquid scintillaton counting.

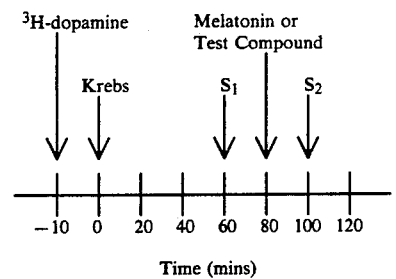

In controls, when two periods of field stimulation are applied, at 60 (S$_1$) and 100 (S$_2$) min, the ratio of the amount of tritium released after S$_2$ to the amount released after S$_1$, i.e., S$_2$/S$_1$, is approximately one. That is, the same cumulative amount of radioactivity is released after each stimulation. However, if a drug, such as melatonin is added after the first stimulation, (but before the second stimulation), then the amount of radioactivity released after the second stimulation is significantly reduced and the S$_2$/S$_1$ ratio becomes less than one. Typically, the inhibition of the release of [$^3$H]dopamine, using 0.1 nM melatonin, is greater than half. If the S$_2$/S$_1$ is plotted as a function of the molar concentration of the amount of added melatonin, it is found that 40 pM melatonin will inhibit [$^3$H]dopamine release by 50%. Dubocovich, M. L., J. Pharmacol. Exp. Ther., 246:902-904 (1988).

The inhibition of [$^3$H]dopamine overflow (the percentage of total tissue radioactivity released by field stimulation above the spontaneous release levels, expressed as the ratio $S_2/S_1$) is plotted as a function of the molar concentrations of the test compound (logarithmic scale). The $IC_{50}$ values were determined graphically from these concentration effect curves (not shown) and are given in Table 3. These results demonstrate that compounds AH 001, AH 002, AH 011, AH 013, AH 015, AH 017, AH 025 and AH 027 are melatonin agonists. Test compounds that show no inhibition of the calcium-dependent release of 3H-dopamine when added alone before $S_2$, are assayed as melatonin receptor antagonists (See Example 25).

TABLE 3

| Compound | Inhibition of [³H]dopamine release from rabbit retina | |
|---|---|---|
| | $IC_{50}(nM)^{(a)}$ | % Maximal Inhibition[b] |
| Melatonin | 0.040 | 80 |
| AH 001 | 1.4 | 80 |
| AH 002 | 0.482 | 80 |
| AH 005 | 52.2 | 50 |
| AH 006 | 8.13 | 70 |
| AH 007 | 10 | 40 |
| AH 008 | ND | ND |
| AH 009 | ND | ND |
| AH 010 | ND | ND |
| AH 011 | 1.3 | 80 |
| AH 013 | 1.18 | 80 |
| AH 014 | 7.94 | 80 |
| AH 015 | 2.51 | 80 |
| AH 016 | >1,000 | 0 |
| AH 017 | 0.063 | 75 |
| AH 018 | ND | ND |
| AH 019 | ND | ND |
| AH 020 | ND | ND |
| AH 023 | NE | ND |
| AH 024 | NE | ND |
| AH 025 | 4 | 70 |
| AH 026 | NE | ND |
| AH 027 | 13 | 65 |
| AH 028 | 16 | 60 |
| AH 029 | 10 | 70 |

[a]$IC_{50}$ values represent the concentration of test compound necessary to inhibit the release of ³H-dopamine by 50%.
[b]Percent maximal inhibition of ³H-dopamine release achieved with 1 μM concentration of test compound.
ND = not determined
NE = no effect

EXAMPLE 25

Assay to Acertain Which Test Compounds Antagonize the Melatonin-Induced Inhibition of [³H]-dopamine Release from Rabbit Retina Membranes Melatonin receptor antagonists are expected to prevent the inhibition of the calcium-dependent release of [³H]dopamine elicited by melatonin from rabbit retina. Dubocovich, M. L., *J. Pharmacol. Exp. Ther.*, 246:902 (1988).

Compounds that show competition for 2-[¹²⁵I]iodomelatonin binding in chicken retinal membranes (Table 2) and show no inhibition of the calcium-dependent release of [³H]-dopamine when added alone before $S_2$ are tested for activity as melatonin receptor antagonists. (See Example 24).

To determine whether a compound is an antagonist of the melatonin-induced inhibition of [³H]dopamine release, the test compound is added before $S_1$ and remains present until the end of the experiment. Melatonin (either 0.01, 0.1, 1.0, 10, or 100 nM) is then added after $S_1$, but before $S_2$.

Typically, the rabbit retina tissues preincubation with [³H]-dopamine for 10 minutes is followed by a superfusion with Krebs solution at time equal zero. At time equal 20 minutes the test compound of interest is added. At time equal 60 minutes $S_1$ is applied. Melatonin is added 20 minutes after $S_1$. $S_2$ is applied 20 minutes after the addition of melatonin.

This relative time sequence is shown below:

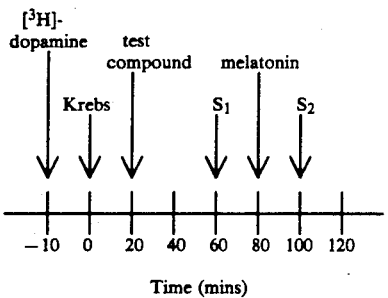

For the control, no test compound is added and melatonin is added before $S_2$; this reduces the calcium-dependent release of [³H]dopamine resulting in an $S_2/S_1$ ratio of less than one. For example, in this particular experiment, using 0.1 nM melatonin gave an $S_2/S_1$ ratio of 0.52; while using 1 nM melatonin gave an $S_2/S_1$ ratio of 0.31.

As noted above, to determine whether a test compound has melatonin antagonist activity, the compound is added 40 minutes before $S_1$ and remains present throughout $S_1$ and $S_2$. Approximately 20 minutes after $S_1$, melatonin is added and remains present throughout $S_2$. If a compound is an antagonist to melatonin activity, higher concentrations of melatonin are needed to attain the $S_2/S_1$ ratios obtained with melatonin in the absence of an antagonist. For test compounds AH 023, AH 024, and AH 026, $S_2/S_1$ ratios closer to unity were obtained (Table 4). These results demonstrate that these compounds do antagonize the melatonin-induced inhibition of [³H]dopamine release in rabbit retina.

The ratio $S_2/S_1$ can be plotted as a function of the molar concentrations of the test compound used (logarithmic scale). The concentration effect curves, obtained in the presence of 0.1 μM and 1 μM of either AH 023 or AH 024 (data not shown) show a shift to the right compared to the curve obtained with melatonin alone. In other words, the $IC_{50}$ value obtained for melatonin alone is a lower molar concentration than obtained in the presence of the test compound, i.e., more melatonin is required to inhibit [³H]dopamine release in the presence of these antagonist compounds.

TABLE 4

| Melatonin Concentration: | Antagonism of melatonin-induced inhibition of [³H]dopamine release from rabbit retina | | |
|---|---|---|---|
| | $S_2/S_1$ | | |
| | 0.1 nM | 1 nM | 10 nM |
| Melatonin[f] | 0.52 ± 0.09[a](4) | 0.31 ± 0.06[a](6) | 0.30 ± 0.03(3) |
| AH 023[e] | | | |
| 0.01 μM | 0.69 ± 0.11(6) | 0.30 ± 0.04(6) | ND |
| 0.1 μM | ND | 0.73 ± 0.04[c](6) | 0.37 ± 0.06(6) |
| 1 μM | 1.02 ± 0.03[b](2) | 0.92 ± 0.07[c](2) | 0.69 ± 0.03[d](3) |
| AH 024[e] | | | |
| 0.1 μM | 1.01 ± 0.07[b](3) | 0.76 ± 0.01[c](6) | 0.25 ± 0.01(3) |
| 1 μM | ND | 0.91 ± 0.06[c](3) | 0.61 ± 0.01[d](3) |
| AH 026[e] | | | |
| 0.1 μM | 1.06 ± 0.06[b](3) | 0.91 ± 0.05[c](3) | 0.53 ± 0.08[d](2) |

TABLE 4-continued

Antagonism of melatonin-induced inhibition of [$^3$H]dopamine release from rabbit retina

| Melatonin Concentration: | $S_2/S_1$ | | |
|---|---|---|---|
| | 0.1 nM | 1 nM | 10 nM |
| 1 μM | ND | 1.08 ± 0.03$^c$(3) | 0.94 ± 0.03$^d$(3) |

$^{(a)}$p < 0.05 when compared with control ($S_2/S_1$ ratio = 0.98 ± 0.05, N = 14).
$^{(b)}$p < 0.05 when compared with melatonin 0.1 nM.
$^{(c)}$p < 0.05 when compared with melatonin 1 nM.
$^{(d)}$p < 0.05 when compared with melatonin 10 nM.
$^{(e)}$test compounds in the concentrations indicated were added 40 minutes before $S_1$, and remained present through the experiment; melatonin (either 0.1 nM; 1 nM; or 10 nM; as indicated) was added 20 mins after $S_1$.
$^{(f)}$melatonin control with no test compound added.

EXAMPLE 26

The compounds of the invention have melatonin agonist/antagonist activity and are expected to have utility in the treatment of disorders associated with circadian or seasonal rhythyms and/or associated with abnormal melatonin levels in the body and/or associated with processes regulated by melatonin.

Melatonin has been implicated in the regulation of various neural and endocrine processes that are cued by the daily change in photoperiod. These include the regulation of seasonal effects on reproduction, body weight, metabolism, and coat color in photoperiodic mammals such as sheep and hamsters (Darrow, J. M., et al., *J. Biol. Rhythms.*, 1:39-54 (1985); Tamarkin, L., et al., *Science*, 227:714-720 (1985); the control of circadian rhythms in birds and reptiles (Menaker, M., *Vertebrate Circadian Systems*, (Berlin:Springer-Verlag) 1-11 (1982); Underwood, H., et al., *Physiol. Behav.*, 35:267-270 (1985)), and the modulation of retinal physiology (Iuvone, P. M., *The retina:A Model for Cell Biology Studies*, (London:Academic) 2:1-72 (1986); Besharse, J. C., *Progress in Retinal Research*, (Oxford:Pergamon) 1:81-124 (1982)). There is also evidence for photoperiodic and melatonin mediated control of cell cancer growth. Stanberry, et al., *Endocrinol.*, 113:469-475 (1983). In addition, melatonin was shown to augment the immune response. Maestroni, et al., *Clin. Exp. Immunol.*, 68:384-391 (1987).

Melatonin also has been implicated in a variety of brain functions and neuroendocrine changes, with a main site of action at the level of the hypothalamic-pituitary axis (Cardinali, *Endocrinol. Rev.*, 2:327-346 (1981); and Minneman, et al., *Life Sci.*, 17:1189-1200 (1975)). Abnormal plasma melatonin levels in humans has been associated with psychiatric illnesses (Jimerson, et al., *Life Sci.*, 20:1501-1508 (1977); Smith, et al., *J. Pharm. Pharmacol.*, 31:246-248 (1979); and Ferrier, et al., *Clin. Endocrinol.*, 17:181-187 (1982), with patients with pinealoma (Wetterberg, *J. Neural Transm.*, 13:289-310 (1978)) and with breast cancer (Tamarkin, et al., *Science*, 216:1003-1005 (1982)).

Melatonin may be effective in synchronizing disturbed circadian rhythms in mammals, including humans (Redman, J., et al., *Science*, 219:1089-1091 (1983); Cassone, V. M., et al., *J. Biol. Rhythms*, 1:219-229 (1986); Arendt, J., et al., *Br. Med. J.*, 292:1170 (1986)). For example, sleep/wake cycle disturbances, caused for example by jet lag (which results from rapid flight across several time zones) or caused by working on night shifts, and the subsequent desynchronization of circadian rhythms can be treated by administration of melatonin at scheduled times (Arendt, J., et al., *Br. Med. J.*, 292:1170 (1986)).

Changes in melatonin levels have also been shown at different stages of the menstrual cycle, with different seasons (Birau, N., Melatonin-current status and perspectives, (Oxford:Pergamon) 297-326 (1981); and Kauppila, A., et al., *J. Clin. Endocrinol. & Metab.*, 65:823-828 (1987)), and also with age (Iguchi, H., et al., *J. Clin. Endocrinol. & Metab.*, 55:27-29 (1982). Changes in melatonin levels have been associated with various pathological states and the mode of action of various therapeutic agents (Birau, N., Melatonin-current status and perspectives, (Oxford:Pergamon) 297-326 (1981). Certain neuroendocrine effects of melatonin in mammals, which include changes in gonadal function and pituitary hormone secretion, appear to be mediated to some extent by the action of melatonin on the brain.

Exposure of animals to light, which inhibits the synthesis of melatonin, or removal of the pineal gland are methods classically used to antagonize the physiological effects of endogenous melatonin (Darrow, et al., *J. Biol. Rhythms*, 1:39-54 (1985); and Tamarkin, et al., *Science*, 227:714-720 (1985)).

Recently, several groups of investigators have used bright light to treat chronobiologic disorders, e.g., seasonal affective disorders (SAD), sleep disorders, and symptoms such as drowsiness and fatigue associate with disturbances in sleep/wake cycles, in humans (Lewy, et al., *Proc. Soc. Exp. Biol. Med.*, 183:11-18 (1986); Lewy, et al., *Science*, 235:352-354 (1987); and Rosenthal, et al., *Arch. Gen. Psychiatric*, 41:72-80 (1984)). If the therapeutic effects of light are related to the suppression of melatonin secretion, melatonin receptor antagonists of the invention are expected to be useful in treating chronobiologic disorders involving changes in the pattern of melatonin secretion.

Administration of melatonin at scheduled times is effective in entraining and synchronizing circadian rhythms regulated primarily by the hypothalamic suprachiasmatic nuclei (Underwood, H., et al., *Physiol. Behav.*, 35:267-270 (1985); Redman, J., et al., *Science*, 219:1089-1091 (1983); and Cassone, V. M., et al., *J. Biol. Rhythms*, 1:219-229 (1986)). In addition, pineal melatonin appears to regulate several neuroendocrine functions such as sleep (Birkland, A. J., *Neuroendocrinology*, 34:126-131 (1982)), thyroid hormone, secretion (Vriend, J., *Med. Hypotheses*, 4:376-387 (1978)) growth hormone release (Smythe, G. A., et al., *Nature (London)*, 244:230-231 (1973)) and intraocular pressure (Krauss, G., et al., *Inv. Ophthalm. Vis. Sci.*, Vol. 26, Abst. 49 (1988)) in humans. A melatonin receptor antagonist, by blocking the melatonin receptor in target tissues, would be expected to mimic the effects of light and to be more effective than pinealectomy in antagonizing the effects of endogenous melatonin inasmuch as this hormone is also secreted by extrapineal tissues (Cardinali, D. P., *Endocrinol. Rev.*, 2:327-346 (1981)).

It is also anticipated that compounds of the invention will be useful in the treatment of various psychiatric disorders related to altered melatonin function or influenced by melatonin and circadian rhthyms, e.g., affective disorders (mania and depression), alcoholism, stress, epilepsis, convulsions, anxiety, tremors induced by idiophatic parkinsonism, and adventitious movements induced by L-dopa movements; and in the treatment of various neuroendocrine disorders related to altered melatonin function or influenced by melatonin and biological rhythms (e.g., peptic ulceration, psoriasis, hair growth, and body weight) particularly relating to regulation of reproductive maturation and function, e.g., idiopathic delayed puberty, sudden infant death (SID), premature labor, infertility, antifertility, premenstrual syndrome, and sexual dysfunction (i.e., impotence and decreased orgasmic activity). It is also expected that compounds of the invention can be used to manipulate the breeding cycles, body weight, coat color and oviposition in animals.

Further, it is anticipated that the compounds of the invention will find utility in localizing melatonin receptors. For example, compounds of the invention can be suitably labelled (e.g., with fluorescent groups or radioactive or non-radioactive isotopes) to serve as markers for both in vitro and in vivo analyses of for example, tissue distribution of melatonin receptors.

The foregoing illustrative examples relate to novel compounds having melatonin receptor agonist/antagonist activities, in particular substituted 2-amido tetralin derivatives; as well as to pharmaceutical preparations comprising such compounds; and methods for using these compounds as therapeutic and diagnostic reagents. While the present invention has been described in terms of specific compounds, compositions, and methods, it is understood that variations and modifications will occur to those skilled in the art upon consideration of the present invention.

For example, it is envisioned that various other substituted 2-amido-tetralin derivatives, will also be effective according to the present invention.

Although the preferred compounds are: 8-methoxy-2-acetamido-tetralin; 8-methoxy-2-propionamidotetralin; 2-chloroacetamido-tetralin; 8-methoxy-2-n-butyramido-tetralin; 8-methoxy-2-cyclopropanecarbonylamido-tetralin; 8-methoxy-2-chloroacetamido-tetralin; 4-phenyl-2-acetamido-tetralin; 4-phenyl-2-propionamidotetralin; 4-benzyl-2-acetamido-tetralin; and 4-phenyl-2-chloroacetamido-tetralin; and 4-benzyl-2-propionamidotetralin; it is not intended to preclude others such as: a) 8-methoxy-4-phenyl-2-acetamido-tetralin; b) 8-methoxy-4-phenyl-2-propionamido-tetralin; c) 8-methoxy-4-benzyl-2-acetamido-tetralin; and d) 8-methoxy-4-benzyl-2-propionamido-tetralin, which, based on structure activity relationships are predicted to be very potent melatonin receptor antagonists (a, b) or potent melatonin receptor agonists (c, d); or any other effective substituted 2-amido-tetralin amide derivative from being included in the scope of the present invention.

Numerous modifications and variations in the invention as described in the above illustrative examples are expected to occur to those skilled in the art and consequently only such limitations as appear in the appended claims should be placed thereon.

Accordingly it is intended in the appended claims to cover all such equivalent variations which come within the scope of the invention as claimed.

What is claimed is:

1. Compounds of the formula:

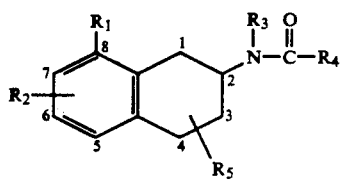

wherein:

$R_1$ is hydrogen, halogen, amino, amido, a $C_{1-4}$ alkyl, $C_{1-4}$ alkoxyl, or $C_{1-4}$ alkoxyl-$C_6$-aryl;

$R_2$ is hydrogen, halogen, amino, amido, $C_6$ aryl, mono- or di- $C_{1-4}$ alkylamino, $C_{1-4}$ alkyl-$C_6$-aryl, or $C_{1-4}$ alkoxyl-$C_6$-aryl, or $C_{1-4}$ alkyl, $C_{2-4}$ alkenyl, $C_{2-4}$ alkynyl, $C_{1-4}$ alkoxyl;

$R_3$ is hydrogen, $C_6$ aryl, $C_{1-4}$ alkyl-$C_6$-aryl, or $C_{1-4}$ alkyl, $C_{2-4}$ alkenyl, or $C_{2-4}$ alkynyl;

$R_4$ is $C_6$ aryl, $C_{1-4}$ alkyl-$C_6$-aryl, or $C_{1-4}$ alkyl, halo-$C_{1-4}$ alkyl, or $C_{3-6}$ cycloalkyl;

$R_5$ is hydrogen, halogen, oxo, $C_6$ aryl, $C_{1-4}$ alkyl-$C_6$-aryl, or $C_{1-4}$ alkyl;

wherein aryl substitutents of $R_2$, $R_3$, $R_4$, and $R_5$ may optionally be halogen, hydroxyl, amino, mono- or di- $C_{1-4}$ alkylamino, or $C_{1-4}$ alkyl or $C_{1-4}$ alkoxyl substituted, provided that when $R_1$ is methoxy, and $R_2$, $R_3$, and $R_5$ are hydrogen, $R_4$ is not methyl.

2. The compounds according to claim 1 wherein said alkoxyl is methoxyl.

3. The compounds according to claim 1 provided that when said $R_1$ is alkoxyl, $R_2$ is not alkoxyl.

4. The compounds according to claim 1 wherein said $R_4$ is methyl, chloromethyl, ethyl, propyl, cyclopropyl, n-butyl, iso-butyl, phenyl, or benzyl.

5. The compounds according to claim 1 wherein said $R_5$ is phenyl or benzyl.

6. The compounds according to claim 1 which are:
8-methoxy-2-propionamido-tetralin;
2-chloroacetamido-tetralin;
8-methoxy-2-n-butyramido-tetralin;
8-methoxy-2-cyclopropanecarbonylamidotetralin;
8-methoxy-2-chloroacetamido-tetralin;
4-phenyl-2-acetamido-tetralin;
4-phenyl-2-propionamido-tetralin;
4-benzyl-2-acetamido-tetralin;
4-phenyl-2-chloroacetamido-tetralin; and
4-benzyl-2-propionamido-tetralin.

7. A pharmaceutical composition for use in treatment of disorders associated with abnormal melatonin activity in an organism, said composition comprising a pharmaceutically acceptable solvent, diluent, adjuvant or carrier and, as the active ingredient, from about 0.001 mg to about 100 mg per kg of body weight of said organism of a compound of the formula:

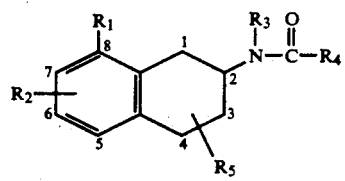

wherein:

$R_1$ is hydrogen, halogen, amino, amido, a $C_{1-4}$ alkyl, $C_{1-4}$ alkoxyl, or $C_{1-4}$ alkoxyl-$C_6$-aryl:

$R_2$ is hydrogen, halogen, amino, amido, $C_6$ aryl, mono- or di- $C_{1-4}$ alkylamino, $C_{1-4}$ alkyl-$C_6$-aryl, or -$C_{1-4}$ alkoxyl-$C_6$-aryl, or $C_{1-4}$ alkyl, $C_{2-4}$ alkenyl, $C_{2-4}$ alkynyl, $C_{1-4}$ alkoxyl;

$R_3$ is hydrogen, -$C_6$ aryl, $C_{1-4}$ alkyl-$C_6$-aryl, or $C_{1-4}$ alkyl, $C_{2-4}$ alkenyl, or $C_{2-4}$ alkynyl;

$R_4$ is $C_6$ aryl, $C_{1-4}$ alkyl-$C_6$-aryl, or $C_{1-4}$ alkyl, halo-$C_{1-4}$ -alkyl, or $C_{3-6}$ cycloalkyl;

$R_5$ is hydrogen, halogen, oxo, $C_6$ aryl, $C_{1-4}$ alkyl-$C_6$-aryl, or $C_{1-4}$ alkyl;

wherein aryl substitutents of $R_2$, $R_3$, $R_4$, and $R_5$ may optionally be halogen, hydroxyl, amino, mono- or di- $C_{1-4}$ alkylamino, or $C_{1-4}$ alkyl or $C_{1-4}$ alkoxyl substituted.

* * * * *